US005627172A

United States Patent [19]

Almada et al.

[11] Patent Number: 5,627,172
[45] Date of Patent: May 6, 1997

[54] METHOD FOR REDUCTION OF SERUM BLOOD LIPIDS OR LIPOPROTEIN FRACTION

[75] Inventors: Anthony Almada, Aptos; Edward Byrd, Pacific Grove, both of Calif.

[73] Assignee: Natural Supplement Association, Incorporated, Golden, Colo.

[21] Appl. No.: 206,089

[22] Filed: Mar. 4, 1994

[51] Int. Cl.$^6$ .......................... A61K 31/66; A61K 31/22; A61K 31/195

[52] U.S. Cl. .......................... 514/120; 514/551; 514/564; 514/824

[58] Field of Search .................... 514/120, 551, 514/564, 824

[56] References Cited

U.S. PATENT DOCUMENTS

| 5,166,142 | 11/1992 | Moss et al. | 514/54 |
| 5,219,846 | 6/1993 | Bru et al. | 514/118 |
| 5,254,549 | 10/1993 | Gold et al. | 514/247 |

OTHER PUBLICATIONS

Balsom, et al., *Creatine Supplementation and Dynamic High–Intensity Intermittent Exercise*, Scand. J. Med. Sci. Sports 1993, 3:143–149.

Greenhaff, et al., *Influence of Oral Creatine Supplementation of Muscle Torque During Repeated Bouts of Maximal Voluntary Exercise In Man*, Clinical Science (1993) 84, 565–571 (Printed in Great Britain).

Sipilä, et al. *Supplementary Creatine As A Treatment For Gyrate Atrophy Of The Choroid And Retina*, N. Eng. J. Med., Apr. 9, 1981, 867–870.

*Primary Examiner*—Kimberly Jordan
*Attorney, Agent, or Firm*—Klaas, Law, O'Meara & Malkin, P.C.

[57] ABSTRACT

A method is disclosed for lowering the concentration of a serum lipid or lipoprotein component in a mammal, including the step of administering to a mammal in need of such treatment a hypolipidemic, therapeutically effective amount of at least one creatine derivative.

15 Claims, No Drawings

METHOD FOR REDUCTION OF SERUM BLOOD LIPIDS OR LIPOPROTEIN FRACTION

FIELD OF THE INVENTION

The present invention relates to a therapeutic method for reducing at least one serum lipid or lipoprotein fraction in a mammal, in particular a human, in need of such therapy.

BACKGROUND OF THE INVENTION

Cholesterol reduction is of great concern to patients suffering from conditions such as cardiovascular disease and atherosclerosis. Elevated cholesterol and low density lipoprotein-cholesterol (LDL-C) in particular are targets for cholesterol reduction therapy. See, for example, the guidelines of the National Cholesterol Education Program's Expert Panel on Detection, Evaluation and Treatment of High Blood Cholesterol in Adults, as reported in Arch. Intern. Med. 148, 36 (1988).

Present therapeutic guidelines include the recommendation that cholesterol-lowering drugs should be considered when cholesterol and LDL-C levels remain significantly elevated after six months of appropriate dietary therapy. For example, see "National Education Program's Working Group Report on the Management of Patients with Hypertension and High Blood Cholesterol," Ann. of Intern. Med. 114, 224 (1991).

Numerous hypolipidemic agents (i.e., agents for reducing serum lipid concentration) are presently known. These include bile acid sequestrants (e.g., cholestyramine, colestipol), nicotinic acid, probucol, fibric acid derivatives (e.g., gemfibrozil, clofibrate), HMG-CoA reductase inhibitors (lovastatin, pravastatin, simvastatin) and omega-3 fatty acids found in various fish oil supplements.

However, many of the known agents have been associated with side effects that can deter or preclude their usage by many patients. Additionally, combination therapy can magnify the incidence of side effects in treated individuals. For example, cholestyramine and colestipol are associated with constipation and abdominal discomfort. Bile acid sequestrants also can reduce absorption of fat-soluble vitamins and can also interact with other drugs in the gut, rendering the drugs unabsorbable. Probucol, clofibrate and gemfibrizol can cause diarrhea, abdominal pain and nausea, and the first two agents have been associated with arrhythmias. Some bile acid sequestrants and binding resins, fibric acid derivatives, and HMG-CoA reductase inhibitors have been implicated in instances of acute hepatitis and liver damage. HMG-CoA reductase inhibitors have been associated with induced myopathy in some populations, and can also lower serum levels of ubiquinone, an essential bioenergetic component in cardiac and skeletal muscles. Niacin, especially in sustained release form, can induce chemical hepatitis. Moreover, the typically large dosages required can cause vigorous skin vasodilation or flushing, and thus adversely affect patient compliance.

Attempts have been made to provide hypolipidemic agents having fewer and/or less severe side effects. For example, U.S. Pat. No. 5,166,142 discloses the use of type IA antiarrhythmic agents, such as quinidine, procainamide or disopyramide or their pharmaceutically acceptable salts as hypolipidemic agents. U.S. Pat. No. 5,254,549 reveals the use of certain BHT ether compounds as hypolipidemic agents.

A continuing need exists for new agents which are effective in lowering serum lipids and lipoprotein fractions, such as total cholesterol, triglycerides, very low density lipoprotein cholesterol (VLDL-C) or LDL-C.

SUMMARY OF THE PREFERRED EMBODIMENTS

In accordance with one aspect of the present invention, there has been provided a method to lower at least one serum lipid or lipoprotein component, which comprises the step of administering to a mammal in need of such treatment a therapeutically effective amount of a creatine derivative or combination of creatine derivatives. The serum lipid or lipid component is more specifically selected from the group consisting of cholesterol and LDL-C.

Generally, the creatine derivative is a compound containing creatine or a creatine based compound. In a preferred embodiment, the creatine derivative is selected from the group consisting of creatine monohydrate, creatine hydrochloride, creatine phosphate and mixtures thereof. The selected compound(s) is advantageously administered orally in an amount from about 1 to 30 grams/day, more particularly about 5 to 20 grams/day. Administration of the creatine derivative according to the invention affords reduction in the concentration of at least one lipid or lipoprotein component of at least about 5%, and in particular at least 7 to 25%.

In accordance with another aspect of the present invention, a composition is provided comprising a hypolipidemic, therapeutically effective amount of a creatine derivative, that is, an amount sufficient to lower the level of at least one serum lipid or lipoprotein component.

In accordance with still another aspect of the present invention a kit is provided for use in the foregoing method. The kit comprises a pre-measured amount of a soluble composition comprising a hypolipidemic, therapeutically effective amount of a creatine derivative, and a container adapted to receive a preselected amount of a pharmaceutically acceptable liquid vehicle.

Other objects, features and advantages of the present invention will become apparent to those skilled in the art from the following detailed description. It is to be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications.

DETAILED DESCRIPTION OF THE PREFERRED EMBODIMENTS

Creatine is a naturally occurring guanidine-derived compound, which, in its phosphorylated form, functions in the maintenance of cellular ATP homeostasis. Creatine and its associated phosphotransferase, phosphocreatine kinase, play an important role in energy provision in muscle and other tissues. Humans, as well as other mammals, synthesize creatine endogenously, and also obtain creatine from normal intake of dietary animal products.

It was previously known to administer creatine or creatine derivatives as ergogenic aids in order to increase muscular performance (Balsom et al., Scand. J. Med. Sci. Sports, 3:143–149, 1993; Greenhaff, et al., Clin. Sci. 84:565, 1993), treat gyrate atrophy of the choroid and retina (Sipiläet al., New England J. Med., 304: 867–870, 1981), and to treat muscular dystrophy and cardiac functional impairment. It has now surprisingly been discovered that administration of creatine derivatives such as creatine monohydrate to a mammal leads to a reduction in the concentration of at least one serum lipid or lipoprotein fraction. When administered in accordance with a regimen as described herein, creatine therapy leads to a reduction of at least about 5% in the serum concentration of at least one lipid or lipoprotein fraction.

Creatine hypolipidemic therapy according to the invention overcomes the deficiencies of the known therapeutic methods. Use of creatine derivatives as hypolipidemic agents is believed to be free of the side effects that have hampered previous methods. At present, the only known side effect of the inventive therapy is loose stools in some individuals, a condition which has been observed to be transient and self-limiting.

Creatine derivatives useful according to the inventive method are virtually tasteless and thus are highly palatable to the patient, affording ease of compliance with the therapeutic regimen. Moreover, creatine is only the second hypolipidemic agent to be identified that is both endogenously produced and is also part of the normal diet of mammals. As a result, the range of safety with respect to dosages administered to the patient is very broad, in contrast to the range of safety associated with synthetic or non-endogenously produced hypolipidemic agents. For example, HMG-CoA reductase inhibitors are typically administered in amounts on the order of 80 mg/day. The creatine derivatives used according to the invention are administered in amounts on the order of 62–2000 times greater than the foregoing inhibitors. Indeed, use of the reductase inhibitors, bile acid sequestering agents, fibrate drugs or niacin in large amounts can be toxic or even fatal to the patient, especially when used in combination therapies.

Creatine derivatives useful according to the invention are not known to interact adversely with other drugs, and thus can be administered in combination with other hypolipidemic agents and/or other types of therapeutic agents. Administration of the creatine derivatives according to the invention may, however, be contraindicated for patients suffering from renal complications.

The serum lipid or lipoprotein fraction which is reduced by administration of a creatine derivative according to the inventive method is in particular an "unfavorable" lipid or lipoprotein fraction, such as the LDL fraction or the total cholesterol fraction. Additional fractions such as the VLDL fraction and the triglyceride fraction can also be affected by the inventive therapeutic method. It is noted, however, that the "favorable" high density lipoprotein cholesterol (HDL-C) fraction is unaffected by the inventive method.

Useful creatine derivatives according to the invention include creatine monohydrate, which is most preferred, as well as pharmaceutically acceptable creatine salts or complexes such as creatine hydrochloride or creatine complexes with other acids. Creatine phosphate is another useful creatine derivative for use in the inventive method. The creatine derivatives can be employed alone, or two or more may be combined for administration to the patient.

Preferably, the creatine derivative is administered daily in an amount from about 1 to 30 grams/day, more preferably about 5 to 20 grams/day. The duration of the therapy will be determined by the nature and severity of the patient's condition. Typically, the creatine derivative will be administered on a chronic (indefinite) basis, rather than an acute basis. Therapy continues until a reduction in the serum concentration of at least one lipid or lipoprotein fraction in an amount of preferably at least about 5%, and more preferably at least about 7 to 25%, is achieved.

In accordance with the present invention, the creatine derivative is preferably administered orally. Compositions for oral administration preferably include solid forms such as capsules, tablets, dispersible powders, and granules. These compositions can contain one or more conventional adjuvants, such as sweetening agents, flavoring agents, coloring agents and preserving agents.

Tablets can contain the creatine derivative in a mixture with conventional pharmaceutically acceptable excipients. These include inert carriers, such as calcium carbonate, sodium carbonate, lactose, and talc; granulating and disintegrating agents, such as starch and alginic acid; binding agents such as starch, gelatin acacia; and lubricating agents, such as magnesium stearate, stearic acid and talc. Tablets may be uncoated or coated by known techniques to delay disintegration and absorption in the gastrointestinal tract thereby potentially providing a sustained action over a longer period of time.

Tablets containing the creatine derivative should be prepared by processes which avoid high temperatures, and should also be produced under dry conditions. This is because the creatine derivatives are typically unstable at high temperatures, particularly in the presence of liquids such as water.

Capsules can be prepared using any conventional process, subject to the foregoing limitations on temperature and moisture, and can contain the creatine derivative alone or in admixture with an inert solid carrier, such as calcium carbonate, calcium phosphate, kaolin or cellulose.

Softgels containing the desired creatine derivative can also advantageously be prepared for use according to the inventive method. In preparing softgels, gelatins having low residual moisture content should be used in order to achieve acceptable stability.

In addition to the foregoing solid administration forms, the creatine derivative can be administered in the form of a food item, such as a candy bar. Such food items preferably do not contain an appreciable moisture content or are subject to high temperatures before consumption by the patient.

If desired, the creatine derivatives can also be administered in the form of syrups, elixirs and suspensions. However, since liquid compositions containing the creatine derivative are typically unstable, such compositions should be prepared at approximately the time of intended use and subsequently consumed by the patient. In a preferred embodiment, the selected creatine derivative, prepared in powdered form, is dissolved in a liquid vehicle such as water, or in a beverage such as tea, juice, coffee, etc. The creatine derivative is virtually tasteless, and thus no additional sweetener or flavoring agent is necessary. The powdered creatine derivative will dissolve in a hot liquid when used in the prescribed quantity. In a cold liquid, however, the powdered creatine derivative will typically not completely dissolve, but will remain partially in suspension.

Other useful liquid administration forms, such as suspensions, syrups and elixirs, may contain the creatine derivative in mixture with any of the conventional excipients utilized in the preparation of such compositions. This includes suspending agents such as methylcellulose, tragacanth and sodium alginate; wetting agents such as lecithin, polyoxyethylene stearate or polyoxyethylene sorbidan monoleate; and preservatives.

Kits for the preparation and administration of the creatine derivative in liquid form are also provided according to the invention. Such kits include a premeasured amount of a powdered or granular composition, or a solid composition in soluble form, containing a hypolipidemic, therapeutically effective amount of the desired creatine derivative, together with an appropriately sized container to receive a pharmaceutically acceptable liquid vehicle. The liquid is measured into the container, and the composition is dissolved therein and ingested by the patient.

Although oral administration is preferred, the creatine derivative may also be adapted for other administration forms, such as intravenous, parenteral or intramuscular administration, as well as for enteral administration orally or through mucus membranes such as intranasal, sublingual, buccal or rectal.

The invention will be further described with reference to the following example.

EXAMPLE

Five (5) grams of creatine monohydrate id blended with an appropriate amount of a caloric sweetener (e.g., glucose, 1 gram). This powder/granular mixture is delivered into a chamber containing a soluble liquid (e.g., purified water) immediately before consumption and thereafter mixed vigorously.

Four male subjects participated in a four-week study to determine the effect of creatine monohydrate on serum lipid concentrations. All subjects were in good health, physically fit and free-living (not confined to hospitals). The subjects did not modify their diets or level of physical activity throughout the study period. Each subject ingested 20 grams of creatine monohydrate per day throughout the four-week period. Subjects entered into the laboratory in a fasting state that was greater than 10 hours. Blood was withdrawn and analyzed within 24 hours for a full profile including cholesterol and other lipoproteins. This was done within one week prior to the beginning of the initiation of creatine loadings and then after a four week period of 20 grams of creatine per day.

Averaged results are shown in the following table:

| Lipid fraction | Initial | Final | % Change | P |
| --- | --- | --- | --- | --- |
| Total Cholesterol (TC) | 214 | 176 | 18 | <0.04 |
| HDL-C | 46.6 | 40.8 | 13 | >0.05 |
| LDL-C | 154 | 120 | 22 | <0.05 |
| TC/HDL | 4.6 | 4.3 | 7 | >0.05 |

As shown in the above table, creatine monohydrate therapy had a statistically significant (P<0.05) effect on the serum levels of LDL-C and total cholesterol. The impact of the therapy on HDL-C level was not statistically significant.

What is claimed is:

1. A method for lowering the concentration of a serum lipid or lipid component in a mammal, comprising the step of administering to a mammal in need of such treatment a hypolipidemic, therapeutically effective amount of a creatine derivative or combination of creatine derivatives selected from the group consisting of creatine monohydrate, a pharmaceutically acceptable creatine salt and creatine phosphate.

2. The method of claim 1 wherein said amount is effective to lower the serum concentration of a lipid or lipoprotein fraction selected from the group consisting of total cholesterol, VLDL, triglycerides, and LDL in said mammal.

3. The method of claim 1 wherein said mammal is a human.

4. The method of claim 1 wherein said creatine derivative or combination of creatine derivatives is orally administered.

5. The method of claim 1 wherein said creatine derivative or combination of creatine derivatives is selected from the group consisting of creatine monohydrate, creatine hydrochloride, and creatine phosphate and mixtures thereof.

6. The method of claim 5 wherein said creatine derivative is creatine monohydrate.

7. The method of claim 1 wherein said creatine derivative or combination of creatine derivatives is administered in an amount from about 1 to 30 grams/day.

8. The method of claim 7 wherein said amount is from about 5 to 20 grams/day.

9. The method of claim 1 wherein the amount of serum total cholesterol is lowered by at least about 5%.

10. The method of claim 9 wherein said amount is at least about 7 to 25%.

11. The method of claim 9 wherein the amount of LDL-C is lowered by at least about 5%.

12. The method of claim 11 wherein said amount is at least about 7 to 25%.

13. The method of claim 1 wherein the amount of LDL-C is lowered by at least about 5%.

14. The method of claim 1 where the amount of triglycerides is lowered by at least 5%.

15. A method for lowering the concentration of a serum lipid or lipoprotein component in a warm blooded animal, the method comprising the steps of administering to an animal in need of such treatment an amount of at least one creatine derivative selected from the group consisting of creatine monohydrate, a pharmaceutically acceptable creatine salt and creatine phosphate sufficient to lower the concentration of at least one serum lipid or lipoprotein component.

* * * * *